US00PP34563P2

(12) United States Plant Patent
Kinney

(10) Patent No.: US PP34,563 P2
(45) Date of Patent: Sep. 13, 2022

(54) ***PINUS* TREE NAMED 'MONMEL'**

(50) Latin Name: *Pinus nigra*
Varietal Denomination: MONMEL

(71) Applicant: Monrovia Nursery Company Inc., Azusa, CA (US)

(72) Inventor: Ron D. Kinney, Dayton, OR (US)

(73) Assignee: Monrovia Nursery Inc., Azusa, CA (US)

( * ) Notice: Subject to any disclaimer, the term of this patent is extended or adjusted under 35 U.S.C. 154(b) by 0 days.

(21) Appl. No.: 17/577,574

(22) Filed: Jan. 18, 2022

(51) Int. Cl.
*A01H 7/00* (2006.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
CPC ..... A01H 7/00
See application file for complete search history.

*Primary Examiner* — Kent L Bell
(74) *Attorney, Agent, or Firm* — Cassandra Bright

(57) ABSTRACT

A new and distinct cultivar of *Pinus nigra* named 'MONMEL' is disclosed, characterized by its tight branching structure, slow growth rate, and bright yellow new candle/needles. The new cultivar is a *Pinus*, typically suited for ornamental use.

1 Drawing Sheet

Latin name of the genus and species: *Pinus nigra.*
Variety denomination: 'MONMEL'.

BACKGROUND OF THE INVENTION

The new cultivar is a chance discovery found among a population of seedlings of an unpatented, unnamed variety of *Pinus nigra*, by the inventor Ron D. Kinney. This discovery was made in a seedling bed at a commercial nursery in Dayton Oreg. in June 2008.

Asexual reproduction was first performed by grafting terminal vegetative scions onto unpatented, unnamed, *Pinus nigra* seedling rootstocks in January 2011, at the same nursery in Dayton, Oreg. 'MONMEL' has since produced additional generations and has shown that the unique features of this cultivar are stable and reproduced true to type.

SUMMARY OF THE INVENTION

The cultivar 'MONMEL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MONMEL'. These characteristics in combination distinguish 'MONMEL' as a new and distinct *Pinus* cultivar:

1. Bright yellow new candle/needles.
2. Slow growth rate.
3. Tighter branching structure.

PARENTAL COMPARISON

Plants of the new cultivar 'MONMEL' are similar to the unnamed, unpatented parent variety of *Pinus nigra* in most horticultural characteristics. However, plants of 'MONMEL' differ in the following ways:

1. New variety has bright yellow new candle/needles that eventually turn green. The parent variety has green needles.

COMMERCIAL COMPARISON

Plants of the new cultivar 'MONMEL' are similar to the unpatented, variety *Pinus nigra* 'Frank' in most horticultural characteristics; however, plants of 'MONMEL' differ in the following ways:

1. 'MONMEL' has bright yellow new candle/needles that eventually turn green. This comparator has green needles.
2. New variety has a slightly tighter and more contorted branch structure than this comparator.

BRIEF DESCRIPTION OF THE PHOTOGRAPH

The accompanying photograph illustrates in full color a typical plant of 'MONMEL' grown outdoors in Dayton, Oreg. This plant is approximately 4 years old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 except where general terms of ordinary dictionary significance are used. The following observations and measurements describe 'MONMEL' plants grown outdoors in Dayton, Oreg. Unless noted as values taken from a mature plant, values are taken from a plant approximately 2 years old, grown in a 3-liter pot. The plant has been grafted onto a seedling of *Pinus nigra*. The specimen is approximately 2 years old, grown outdoors in Dayton, Oreg. No artificial light, photoperiodic treatments or chemical treatments were given to the plants. Measurements and numerical values represent averages of typical plant types.

Botanical classification: *Pinus nigra* 'MONMEL'.

Age of the plant described: Values are taken from a 2-year-old specimen, unless noted as a mature tree measurement.

Container size of the plant described: 3-gallon commercial container.

PROPAGATION

Time to rooting: 60 to 90 days at approximately 40°-50° F.

Root description: Woody main roots, colored near RHS Brown 200D. Lateral roots fibrous, very well branched, colored near RHS Grey-Brown 199A.

PLANT

Growth habit: Compact evergreen tree.

Height: Approximately 45 cm.

Plant spread: Approximately 30 cm.

Typical growth rate: Slow for species.

Pinching required: No.

Branching characteristics: Single main stem with approximately 6 to 8 lateral branches on a plant of this age and size. Lateral stems are straight or very slightly curved, rather than acute angle at the point of attachment. Lateral branch angle from the main stem is approximately 75 to 90° from the center of the plant.

Main stem:

*Length*.—Average 32 cm.

*Diameter*.—Approximately 1.5 cm at base, approximately 10 mm at top.

*Color*.—Near RHS Greyed-Green 197C.

*Texture*.—Rough, scaly.

*Strength*.—Very strong and flexible.

Length of lateral branches: Average 6 to 12 cm.

Diameter of lateral branches: Average 7 mm.

Lateral branch shape in cross section: Round.

Lateral branch strength: Very strong, moderately flexible.

Lateral branch color: Near RHS Grey-Brown 199A.

Lateral branch texture: Rough.

Internode length: Average range between 3.0 cm and 4.0 cm.

Candles/new growth:

*Length*.—Average 2 cm.

*Diameter*.—Average 8 mm.

*Shape*.—Conical.

*Color*.—Near Yellow 4B.

FOLIAGE

General description: Needles, held 2 per group.

Leaf:

*Arrangement*.—Radially arranged fascicles, 2 needles per fascicle.

*Type*.—Needle.

*Shape of blade*.—Needle. Flattened triangular.

*Average length*.—Approximately 7.5 cm.

*Average width*.—Approximately 2 mm.

*Apex*.—Acute, not very sharp.

*Base*.—Sessile.

*Fascicle sheath*.—Length: 2 to 3 mm. Width: 3 mm. Color: Near RHS Grey-Brown N199B.

*Attachment*.—Sessile.

*Margin*.—Entire.

*Aspect*.—Needle has a twist and an overall moderate curve.

*Texture of top surface*.—Glabrous.

*Texture of bottom surface*.—Glabrous.

*Fascicle internode length*.—Approximately 5 mm.

*Color*.—Young foliage upper side: Near RHS Yellow 4B. Young foliage under side: Near RHS Yellow 4B. Mature foliage upper side: Near RHS Green 137A. Mature foliage under side: Near RHS Green 137A. Winter foliage upper side: Near RHS Green 137A. Winter foliage under side: Near RHS Green 137A.

*Venation*.—Linear, indistinguishable from leaf blade.

*Fragrance*.—Moderate, distinctive pine scent.

FLOWER

Flowering not observed.

REPRODUCTIVE ORGANS

General description of visible parts: Not observed.

OTHER CHARACTERISTICS

Cone: Not observed.

Drought tolerance and temperature tolerance: USDA Zones 5 through 8. Moderate drought tolerance.

Disease/pest resistance: Neither extra resistance nor susceptibility to the normal pests and diseases of *Pinus* has been observed.

What is claimed is:

1. A new and distinct cultivar of *Pinus nigra* tree named 'MONMEL' as herein illustrated and described.

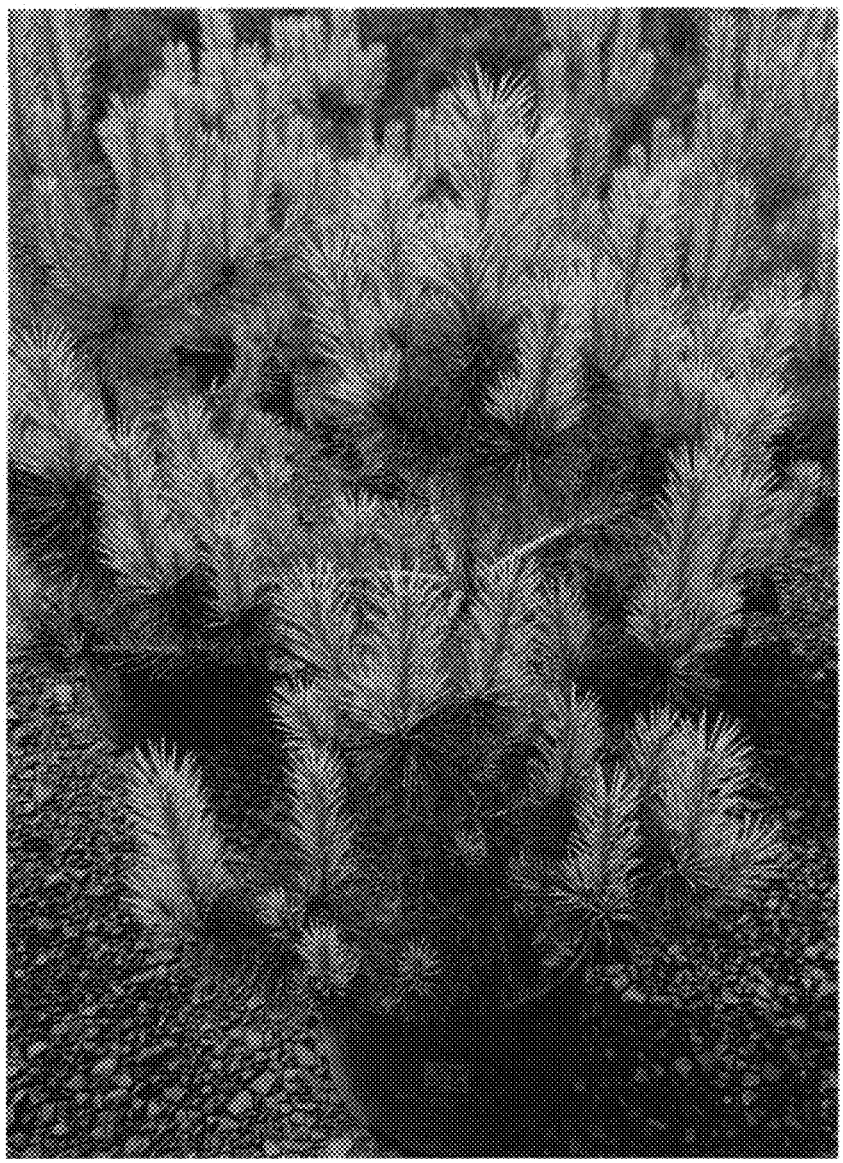

* * * * *